(12) United States Patent
Cao et al.

(10) Patent No.: US 11,457,833 B2
(45) Date of Patent: Oct. 4, 2022

(54) DISCRETE BIOELECTRICAL IMPEDANCE IDENTIFICATION DEVICE

(71) Applicant: BEIJING SMTP TECHNOLOGY CO., LTD., Beijing (CN)

(72) Inventors: Qun Cao, Beijing (CN); Songtao Zhan, Beijing (CN); Jianxiong Shen, Beijing (CN)

(73) Assignee: Beijing SMTP Technology Co., Ltd., Beijing (CN)

( * ) Notice: Subject to any disclaimer, the term of this patent is extended or adjusted under 35 U.S.C. 154(b) by 565 days.

(21) Appl. No.: 16/479,192

(22) PCT Filed: Mar. 27, 2018

(86) PCT No.: PCT/CN2018/080693
§ 371 (c)(1),
(2) Date: Jul. 18, 2019

(87) PCT Pub. No.: WO2018/177290
PCT Pub. Date: Oct. 4, 2018

(65) Prior Publication Data
US 2019/0343419 A1  Nov. 14, 2019

(30) Foreign Application Priority Data
Mar. 31, 2017 (CN) .......................... 201710208391.X

(51) Int. Cl.
*A61B 5/0538* (2021.01)
(52) U.S. Cl.
CPC .... *A61B 5/0538* (2013.01); *A61B 2560/0214* (2013.01); *A61B 2560/0443* (2013.01)
(58) Field of Classification Search
CPC ... A61B 5/053; A61B 5/0538; A61B 2560/00; A61B 2560/02; A61B 2560/0204;
(Continued)

(56) References Cited

U.S. PATENT DOCUMENTS

2005/0119660 A1    6/2005  Maurice et al.
2006/0036188 A1*   2/2006  Hoffman ................. A63B 23/20
                                                                    600/591
(Continued)

FOREIGN PATENT DOCUMENTS

CN    201870718 U    6/2011
CN    103327893 A    9/2013
(Continued)

OTHER PUBLICATIONS

PCT/CN2018/17729, International Search Report dated Jul. 2, 2018, 2 pages.
(Continued)

*Primary Examiner* — Matthew Kremer
*Assistant Examiner* — Om Patel
(74) *Attorney, Agent, or Firm* — Kilpatrick Townsend & Stockton LLP

(57) ABSTRACT

A discrete bioelectrical impedance identification device, comprising a control module (1) and a detection module (2), wherein the control module (1) comprises a control shell (20) and a control processing circuit (21) provided inside the control shell (20); the control shell (20) is provided with conducting strips (201) which are partially exposed out of the control shell (20); the conducting strips (201) are electrically connected to the control processing circuit (21), wherein the detection module (2) comprises a detection shell (23), a probe (231) embedded in one end of the detection shell (23), a power supply (232) embedded in the other end of the detection shell (23), and a conducting needle group (233) partially exposed out of the shell; the control shell (20) is detachably connected to the detection shell (23); when the control shell (20) is firmly connected to the detection shell (23), the conducting needle group (233) abuts against the conducting strips (201); and when the control shell (20) is separated from the detection shell (23), the conducting needle group (233) is separated from the conducting strips (201). The device can improve the utilization rate of the product and reduce the use cost.

9 Claims, 7 Drawing Sheets

(58) Field of Classification Search
CPC ........ A61B 2560/0214; A61B 2560/04; A61B
2560/0406; A61B 2560/0418; A61B
2560/0443; A61B 5/063; A61B 5/0536;
A61B 5/068; A61B 2017/00026; A61B
2017/0003; A61B 17/88; A61B 17/90;
A61B 2017/00477; A61B 2017/0046;
A61B 50/00
See application file for complete search history.

(56) References Cited

U.S. PATENT DOCUMENTS

2007/0112284 A1* 5/2007 Hoffman ............... A61B 5/053
128/905
2007/0213691 A1* 9/2007 Summerer ........... H01R 13/627
606/1
2013/0296734 A1* 11/2013 Bourlion ............ A61B 17/7082
600/547
2016/0000514 A1 1/2016 Ellman

FOREIGN PATENT DOCUMENTS

| CN | 103750895 A | 4/2014 |
| CN | 205144558 U | 4/2016 |
| CN | 106901735 A | 6/2017 |
| CN | 106901736 A | 6/2017 |
| CN | 207821816 U | 9/2018 |

OTHER PUBLICATIONS

PCT/CN2018/080693, "International Preliminary Report on Patentability", dated Oct. 10, 2019, 12 pages.

* cited by examiner

DISCRETE BIOELECTRICAL IMPEDANCE IDENTIFICATION DEVICE

CROSS-REFERENCE TO RELATED APPLICATIONS

This application is a 371 National Stage of International Application No. PCT/CN2018/080693, filed Mar. 27, 2018, which claims priority to Chinese Application No. 201710208391.X (CN), filed Mar. 31, 2017, both of which are hereby incorporated by reference in their entireties for all purposes.

TECHNICAL FIELD

The present disclosure relates to the technical field of medical apparatus, and more particularly, a discrete bioelectrical impedance identification device.

BACKGROUND

In the related art, in surgery operations, especially in spinal surgery and neurosurgery operations, the spine needs to be fixed after the laminectomy. The implant screws used for fixation need to be inserted into the vertebral body along the vertebral pedicle by surgeons. This operation is generally a blind operation, and whether it can succeed or not depends on the surgeons' experiences. Medical accidents caused by screws, which enter the vertebral canal due to misaligned insertion, occur from time to time.

There are two methods that assist in observing the screws: one is to observe the position of the screws by means of intraoperative X-ray fluoroscopy, however, this kind of observation has a disadvantage that it can cause radiation damage to the patient and cannot be used frequently; the other is to detect the closure of nerve roots by the screws through an evoked potential equipment and further determine whether the direction of the screw deviates or not, however, it has disadvantages of relatively long preoperative preparation time, poor measurement accuracy, and relatively expensive evoked potential equipment, which is not standard equipment for all hospital operating rooms.

The identification device based on bioelectrical impedance technology can effectively avoid the shortcomings of the above two methods, which is faster and safer, but the products are mostly designed as one piece, as shown in FIG. 1. Since the device is a battery-powered electronic device, it is not easy to clean and sterilize after use of the product so that it can only be a disposable product, which not only causes a large waste, but also increases the cost of surgery.

SUMMARY

An object of one implementation of the present disclosure is to provide a discrete bioelectrical impedance identification device.

According to one aspect of the present disclosure, it provides a discrete bioelectrical impedance identification device comprising: a control module and a detection module, wherein the control module includes a control shell and a control processing circuit arranged inside the control shell, the control shell is provided with conducting strips which are partially exposed out of the control shell and electrically connected to the control processing circuit; the detection module, which is firmly connected to the control module in a detachable connection manner; wherein the detection module comprises: a detection shell, a probe embedded in one end of the detection shell, and a power supply embedded in the other end of the detection shell; the probe which is partially exposed out of the detection shell and used for collecting signals of electrical impedance characteristics; the detection shell, which has a receiving chamber for receiving the probe therein, allowing itself to sleeve outside the probe, and has, at its end away from the probe, a power supply receiving chamber for receiving the power supply; the detection shell is provided with a conducting needle group on the shell at the end provided with the power supply, the conducting needle group being partially exposed out of the shell and being electrically connected at one end to the power supply; the control shell is firmly connected to the detection shell in a detachable connection manner, wherein when the control shell is firmly connected to the detection shell, the conducting needle group abuts against the conducting strips, and when the control shell is separated from the detection shell, the conducting needle group is separated from the conducting strips.

Further, the detachable connection of the device is one of a snap connection, a transverse insertion connection, or a threaded connection.

Further, when the device uses the snap connection as the detachable connection between the shell and the connecting rod: at its end connected to the detection shell the control rod is provided with a protrusion; at its end connected to the control shell the detection shell is provided with a groove; the groove is matched with the protrusion in size so that the protrusion can be inserted into the groove; the conducting needle group is arranged at the bottom of the groove, and the conducting strips are arranged at the top end of the protrusion, wherein the arranged position of the conducting needle group is matched with the arrangement of the conducting strips so that when the protrusion is inserted into the groove, the conducting needle group can abut against the conducting strips; snapping slots are provided around the control shell at its end connected to the detection shell; snapping claws are provided around the detection shell at its end connected to the control shell; and the snapping claws are matched with the snapping slots in shape and size so that the snapping claws can be engaged with the snapping slots.

Further, when the device uses the transverse insertion connection as the detachable connection between the shell and the connecting rod: at its end connected to the detection shell the control shell is provided with a sliding rail; at its end connected to the control shell the detection shell is provided with a sliding rail slot; the sliding rail is matched with the sliding rail slot in shape and size so that the sliding rail can be snapped into the sliding rail slot; the conducting needle group is arranged at the bottom of the sliding rail slot, and the conducting strips are arranged at the top of the sliding rail, wherein the arranged position of the conducting needle group is matched with the arrangement of the conducting strips so that when the sliding rail is inserted into the sliding rail slot, the conducting needle group can abut against the conducting strips. A snapping claw is provided at one end of the sliding rail slot, and a snapping slot is provided at one end of the sliding rail, wherein the snapping claw is matched with the snapping slot in shape, size and position so that the snapping claw can be engaged with the snapping slot.

Further, when the device uses the threaded connection as the detachable connection between the shell and the connecting rod: at its end connected to the detection shell the control shell is provided with an annular protrusion; at its end connected to the control shell the detection shell is provided with an annular groove; female threads are provided on the outer wall of the annular protrusion, and male threads are provided on the outer wall of the annular groove, wherein the female threads are matched with the male threads so that the annular protrusion can be screwed with the annular groove; the conducting needle group is arranged in the middle of the annular groove; the annular conducting strips are arranged in the middle of the annular protrusion, and the arranged position of the conducting needle group is matched with the arrangement of the conducting strips so that when the annular protrusion is screwed to the annular groove, the conducting needle group can abut against the conducting strips.

According to another aspect of the present disclosure, the detection shell of the device comprises: a power supply shell and a probe shell, wherein the power supply is provided in the power supply shell, and the power supply shell is provided with a conducting dot partially exposed out of the power supply shell, wherein the conducting dot is electrically connected to the power supply. At its end connected to the power supply shell the probe shell is provided with a conducting needle partially exposed out of the probe shell, and the conducting needle is electrically connected at one end to the probe.

The probe shell is firmly connected to the power supply shell in a detachable connection manner. When the probe shell is firmly connected to the power supply shell, the conducting needle abuts against the conducting dot; and when the probe shell is separated from the power supply shell, the conducting needle is separated from the conducting dot.

Further, the detachable connection adopted by the detection shell is one of a snap connection, a transverse insertion connection, or a threaded connection.

Further, when the snap connection is used as the detachable connection between the power supply shell and the probe shell: at its one end connected to the probe shell the power supply shell is provided with a protrusion; at its one end connected to the power supply shell the detection shell is provided with a groove; the groove is matched with the protrusion in size so that the protrusion can be inserted into the groove; the conducting needle is arranged at the bottom of the groove, the conducting dot is arranged at the top end of the protrusion, and the arranged position of the conducting needle is matched with the arrangement of the conducting dot so that when the protrusion is inserted into the groove, the conducting needle can abut against the conducting dot; snapping claws are provided around the groove at its top end, and the protrusion is provided at its back end with snapping slots, wherein the snapping claws are matched with the snapping slots in shape and size so that the snapping claws can be engaged with the snapping slots.

Further, when the transverse insertion connection is used as the detachable connection between the power supply shell and the probe shell, at its end connected to the probe shell the power supply shell is provided with a sliding rail; at its end connected to the power supply shell the probe shell is provided with a sliding rail slot; the sliding rail slot is matched with the sliding rail in shape and size so that the sliding rail can be inserted into the sliding rail slot; the conducting needle is arranged in the middle of the sliding rail slot, and the conducting dot is arranged in the middle of the sliding rail, wherein the arranged position of the conducting needle is matched with the arranged position of the conducting dot so that the conducting needle can abut against the conducting dot when the sliding rail is inserted into the sliding rail slot; the sliding rail slot is provided at its one end with a snapping claw, and the sliding rail is provided at its back end with a snapping slot, wherein the snapping claw is matched with the snapping slot in shape, size and position so that the snapping claw can be engaged with the snapping slot.

Further, when the threaded connection is used as the detachable connection between the power supply shell and the probe shell, at its one end connected to the probe shell the power supply shell is provided with a groove; at its end connected to the power supply shell the probe shell is provided with a protrusion; female threads are provided on the outer circumference of the protrusion, and male threads are provided on a wall of the groove, wherein the female threads are matched with the male threads so that the protrusion can be screwed with the groove; the conducting needle is arranged at the top of the protrusion, the conducting dot is arranged at the bottom of the groove, and the arranged position of the conducting needle is matched with the arrangement of the conducting dot, so that the conducting needle can abut against the conducting dot when the protrusion is screwed into the groove.

Integral bioelectrical impedance identification device in the related art is mostly designed as one piece. Since the probe and the probe shell are in direct contact with human skin, it is inconvenient to clean and sterilize after use so that it can only be a disposable consumable. Since the device is discarded after use, the entire product has to be discarded, which not only causes a large waste, but also increases the cost of surgery.

The discrete bioelectrical impedance identification device of the present disclosure uses the topological electrode to detect the electrical impedance so as to obtain the distribution information of the detected tissues, and uses the multi-channel data to reconstruct the three-dimensional tissues model of the detection site, which can provide a full-view vision for the surgery operation and help the surgeon judge the channel paths of the screws, high resolution and high sensitivity, thereby avoiding pushing and drawing the bit for many times in traditional surgery of vertebral pedicle, saving operation time and improving the success rate of surgery.

Compared with the integral bioelectrical impedance identification device in related art, the present disclosure adopts a discrete bioelectrical impedance identification device, and the detection module is used as a disposable consumable, and is directly discarded after use. The remaining control modules can be continuously used after disinfection. On the one hand, the utilization rate of the product is improved, and the control device can be repeatedly used for many times, which reduces the use cost. On the other hand, the waste is avoided and such products are more environmentally friendly.

REFERENCE NUMERAL

1—control module, 20—control shell, 21—control processing circuit, 201—conducting strip, 2—detection module, 23—probe shell, 231—probe, 232—power supply, 233—conducting needle group, 202—protrusion, 234—groove, 203—snapping slot, 235—snapping claw, 204—sliding rail, 236—sliding rail slot, 205—annular protrusion, 237—annular groove, 206—female thread, 238—male thread, 24—power supply shell, 240—conducting dot, 25—probe shell, 250—conducting needle, 260—silicone sealing ring.

DETAILED DESCRIPTION OF THE EMBODIMENTS

To make the objectives, technical solutions and advantages of one embodiment of the present disclosure clearer, the present disclosure will be further described in detail below in combination with specific embodiments and with reference to the accompanying drawings. It is to be understood that the description is illustrative, not intended to limit the scope of the present disclosure. In addition, descriptions of well-known structures and techniques are omitted in the following description in order to avoid unnecessarily obscuring the concept of the present disclosure.

Figure 1:
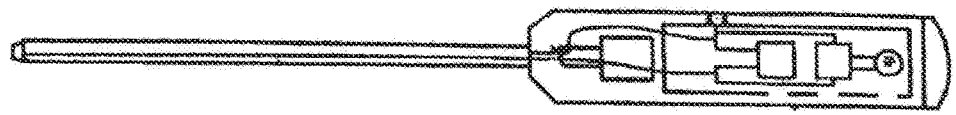
FIG. 1 is a structural schematic view of an integrated bioelectrical impedance identification device of related art.
Figure 2:
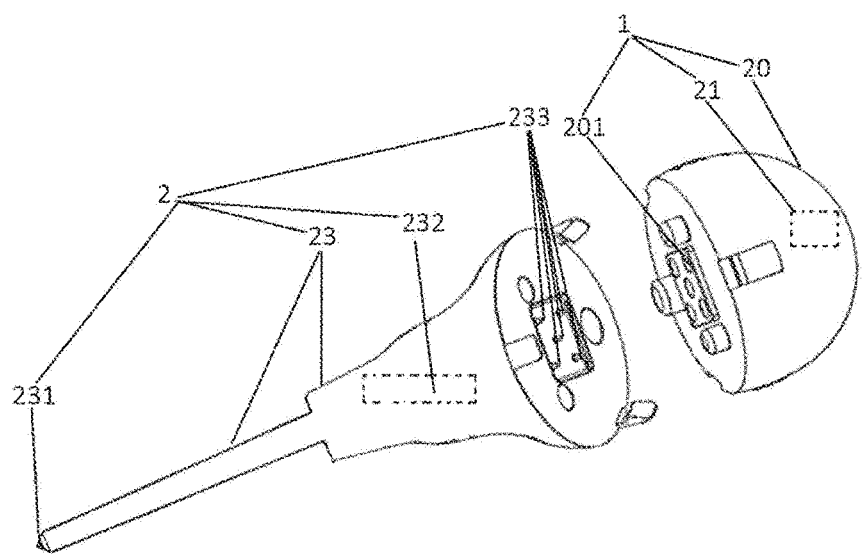
FIG. 2 is an overall structural schematic view of a discrete bioelectrical impedance identification device according to a first embodiment of the present disclosure.

Referring to FIG. 2, it is a structural schematic view of a discrete bioelectrical impedance identification device according to a first embodiment of the present disclosure.

As shown in FIG. 2, the present disclosure provides a discrete bioelectrical impedance identification device comprising: a control module 1 and a detection module 2. The control module 1 and the detection module 2 are firmly connected in a detachable connection manner, so that the control module 1 can be used multiple times.

The control module 1 includes a control shell 20 and a control processing circuit 21 arranged inside the control shell 20. Specifically, the control shell 20 may be in the form of a sphere, a hemisphere, an irregular sphere, or other geometric shape having a receiving space. The control processing circuit 21 is arranged in the receiving space. The control shell 20 is provided with conducting strips 201. The conducting strips 201 are partially exposed outside the control shell 20 and partially embedded in the control shell 20. The conducting strips 201 are composed of at least five conducting strips 201. Specifically, each of the conducting strips 201 is made of conductive material, which specifically, may be copper, iron and other conducting synthetic metals. The conducting strips 201 are electrically connected to the control processing circuit 21 through conducting wires. Specifically, the control processing circuit 21 includes a processor, a signal collector, an alarm, and a wireless communication module. The signal collector is used for performing analog-to-digital conversion on the signal of electrical impedance characteristic. The processor is used to generate control parameters based on the signals of electrical impedance characteristic after the analog-to-digital conversion. The alarm is used for giving a warning by sounds or lights based on the control parameters. The wireless communication module is used for transmitting the signals of electrical impedance characteristic after analog-to-digital conversion.

The detecting module 2 includes a detection shell 23, a probe 231 and a power supply 232, the probe and the power supply being arranged at the opposite ends of the detection shell 23. The detection shell 23 can be in the form of a pyramid, a cylinder, a flat shape, a flat curved rod shape, or other geometric shapes having a receiving space. The probe 231 is partially exposed outside the detection shell 23, partially embedded inside the detection shell 23 and electrically connected to the power supply 232 arranged in the detection shell 23 at the opposite end. Specifically, the power supply 232 may be configured as a disposable battery, a lithium battery, or any other power unit for supplying power. The probe 231 is used for collecting signals of electrical impedance characteristic. The tip of the probe 231 exposed outside the detection shell 23 may be tapered or flat.

A conducting needle group 233 is provided at one end of the detection shell 23 where the power supply 232 is provided, wherein the conducting needle group 233 is partially exposed outside the detection shell 23 and partially embedded in the detection shell 23, and its end embedded in the detection shell 23 is electrically connected to the power supply 232. The conducting needle group 233 is composed of at least five conducting needles. Specifically, each of the conducting needles may be made of conductive material, which specifically, may be copper, iron or other conducting synthetic metals.

The control shell 20 is firmly connected to the detection shell 23 in a detachable connection manner. When the control shell 20 is firmly connected to the detection shell 23, the conducting needle group 233 abuts against the conducting strips 201, and the device starts to work. When the control shell 20 is separated from the detection shell 23, the conducting needle group 233 is separated from the conducting strips 201, and the device stops working.

The detachable connection between the control shell 20 and the detection shell 23 is one of a snap connection, a transverse insertion connection, or a threaded connection.

The present disclosure provides a discrete bioelectrical impedance identification device, which is configured in such a manner that the control module 1 is firmly connected to the detection module 2 in a detachable connection manner. Compared with the integrated undetachable connection of the control module 1 and the detection module 2 of the related art, the detachable connection brings the following benefits:

Firstly: The usage rate of the control module 1 is increased, the use cost is reduced, waste is avoided, and the environment is protected: the control module 1 and the detection module 2 are firmly connected during the operation to complete the operation. After the operation is completed, the control module 1 is separated from the detection module 2, the control module 1 is retained for subsequent use with a new detection module 2, and only the detection module 2 is discarded (the medical device that is in contact with the surgical portion must be disposable due to the need for surgical hygiene).

Secondly: The adaptability of detection modules 2 of different specifications to the control module 1 is realized, and the operation cost and the production cost are reduced: for detection modules 2 of different specifications, the use in combination with the control module 1 can be realized, and the hospital can build bioelectrical impedance identification devices of various specifications by purchasing only a small amount of control modules 1, which greatly saves the operation cost. In addition, in the related art, since the detection module 2 is undetachable from the control module 1, during production, the control module 1 and the detection module 2 must be integrally produced for each electrical impedance identification device. When there are different specifications of the detection modules 2 (due to the need of surgery, probes 231, power supplies 232 and detection shells 23 of different shapes and sizes may be needed), more production lines and production workshops must be used to realize production of different specifications. In the present disclosure, as the control module 1 and the detection module 2 can be detachably separated, the control module 1 and the detection module 2 can be separately produced in the process of production, thereby saving the production lines and the production workshops.

Thirdly: The present disclosure provides three different kinds of detachable connections between the detection module 2 and the control module 1, which can adapt to different surgeons' operating habits and is more humanistic. With an integrated design, the entire device can only be discarded after the surgery is completed, which results in a lot of waste and significantly increases the cost of surgery. The discrete bioelectrical impedance identification device provided by the present disclosure avoids this problem. In addition, the adoption of a variety of connections could not only replace different detection modules 2 to meet various surgical requirements, but also satisfy the surgeons' operating patterns.

Figure 3:
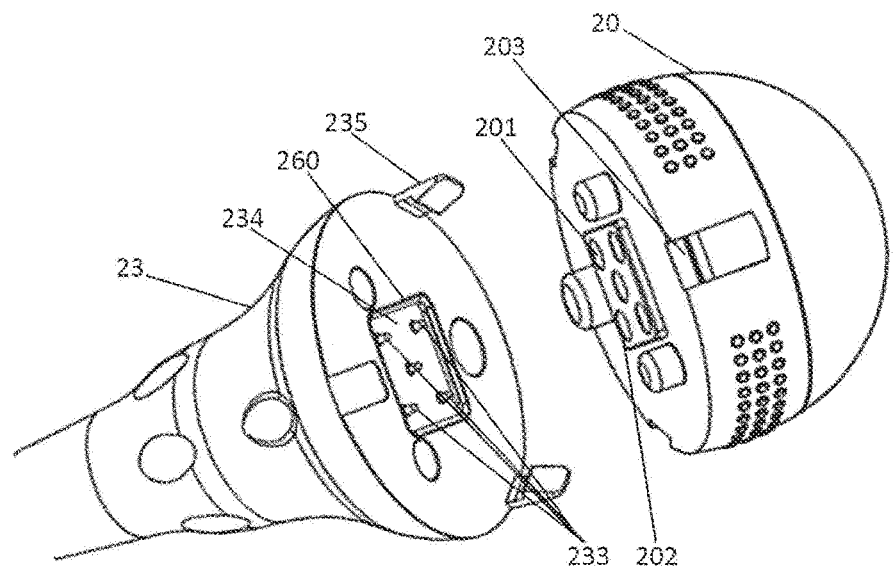
FIG. 3 is a structural schematic view of a discrete bioelectrical impedance identification device according to a second embodiment of the present disclosure.

Referring to FIG. 3, it is a schematic structural view of a discrete bioelectrical impedance identification device according to a second embodiment of the present disclosure.

As shown in FIG. 3, in the embodiment of the present disclosure, when the discrete bioelectrical impedance identification device adopts a snap connection as the detachable connection between the control shell 20 and the detection shell 23, at its end connected to the detection shell 23 the control shell 20 is provided with a protrusion 202. At its end connected to the control shell 20 the detection shell 23 is provided with a groove 234. The groove 234 is adapted to the protrusion 202 in size and shape so that the protrusion 202 can be inserted into the groove 234. The groove 234 and the protrusion 202 may be cylindrical, conical, or of other geometric shapes.

The conducting needle group 233 is arranged at the bottom of the groove 234, the conducting strips 201 are arranged at the top end of the protrusion 202, and the arranged position of the conducting needle group 233 is adapted to the arrangement of the conducting strips 201 so that when the protrusion 202 is inserted into the groove 234, the conducting needle group 233 can abut against the conducting strips 201. At least two snapping claws 235 are arranged around the top end of the groove 234, and at least two snapping slots 203 are provided at the back end of the protrusion 202. The snapping claws 235 are adapted to the snapping slots 203 in size and shape so that the snapping claws 235 can be engaged with the snapping slots 203. Specifically, the snapping claws 235 are provided with at least one snapping tooth, and the snapping tooth is matched with the snapping slot 203 in shape and size.

The protrusion 202 is inserted into the groove 234, the snapping claws 235 are inserted into the snapping slots 203, and the conducting needle group 233 abuts against the conducting strips 201, so that the device can be powered on, starting to work. After use, the snapping claws are separated from the snapping slots 203, the protrusion 202 is drawn out from the groove 234, and the conducting needle group 233 is separated from the conducting strips 201, so that the device is powered off and stops working.

A silicone sealing ring 260 is arranged around the conducting needle group 233 to prevent liquid from entering the interior of the shell to ensure the safety of operational procedure.

Snap connection is adopted, as it is simple and convenient to operate, thereby saving time for connecting. The insertion of the protrusion 202 into the groove 234 has a fixing effect to some extent, thereby preventing the connecting portion from loosening during the operation and avoiding a surgical accident.

Figure 4A:
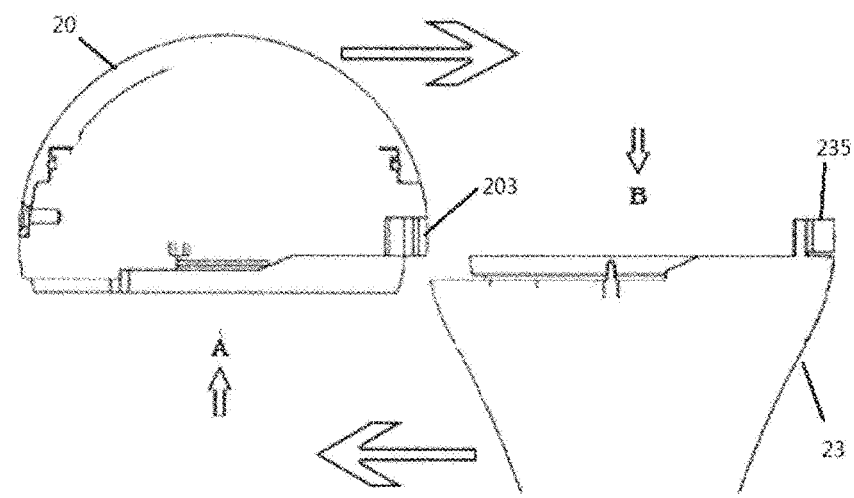
FIG. 4a is a structural schematic view of a discrete bioelectrical impedance identification device according to a third embodiment of the present disclosure.
Figure 4B:
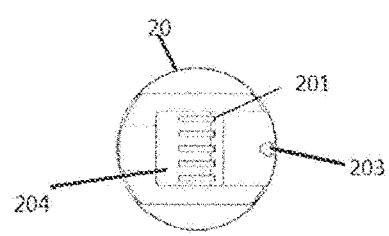
FIG. 4b is a bottom view of a control shell of a discrete bioelectrical impedance identification device according to a third embodiment of the present disclosure.
Figure 4C:
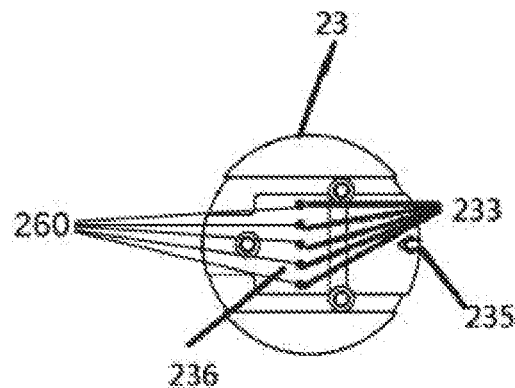
FIG. 4c is a top view of a detection shell of a discrete bioelectrical impedance identification device according to a third embodiment of the present disclosure.

Referring to FIGS. 4a, 4b, and 4c, they are schematic structural views of a discrete bioelectrical impedance identification device according to a third embodiment of the present disclosure.

As shown in FIGS. 4a, 4b, and 4c, in the embodiment of the present disclosure, when the discrete bioelectrical impedance identification device uses a transverse insertion connection as the detachable connection between the control shell 20 and the detection shell 23, at its end connected to the detection shell 23 the control shell 20 is provided with at least one sliding rail 204, and at its end connected to the control shell 20 the detection shell 23 is provided with at least one sliding rail slot 236. The sliding rail slot 236 is matched with the sliding rail 204 so that the sliding rail 204 can be inserted into the sliding rail slot 236.

The conducting needle group 233 is arranged in the bottom middle of the sliding rail slot 236, and the conducting strips 201 are arranged in the top middle of the sliding rail 204. The arranged position and amount of the conducting needle group 233 are matched with the arrangement of the conducting strip 201 so that when the sliding rail 204 is inserted into the sliding rail slot 236, the conducting needle group 233 can abut against the conducting strips 201.

The sliding rail slot 236 is provided at one end with at least one snapping claw 235, while the sliding rail 204 is provided at one end with at least one snapping slot 203. The snapping claw 235 is matched with the snapping slot 203 in shape, size and position so that the snapping claw 235 can be engaged into the snapping slot 203.

The sliding rail 204 slides into the sliding rail slot 236, the snapping claw 235 is snapped into the snapping slot 203, and the conducting needle group 233 abuts against the conducting strips 201, so that the device can be powered on for use. After use of the device, the snapping claw 235 is separated from the snapping slot 203, the sliding rail 204 slides out from the sliding rail slot 236, the conducting needle group 233 is separated from the conducting strips 201, and the device stops working.

A silicone sealing ring 260 is arranged around the conducting needle group 233 to prevent liquid from entering the interior of the shell, ensuring a much safer operational procedure.

Through the transverse insertion connection, on the one hand, a side buckle is designed for fixing in addition to the fixing by the sliding rail 204 and the sliding rail slot 236, which realizes a better fixing effect. On the other hand, the design of the sliding rail 204 and the sliding rail slot 236 makes the detection shell 23 and the control shell 20 easier to align and engage with each other.

Figure 5A:
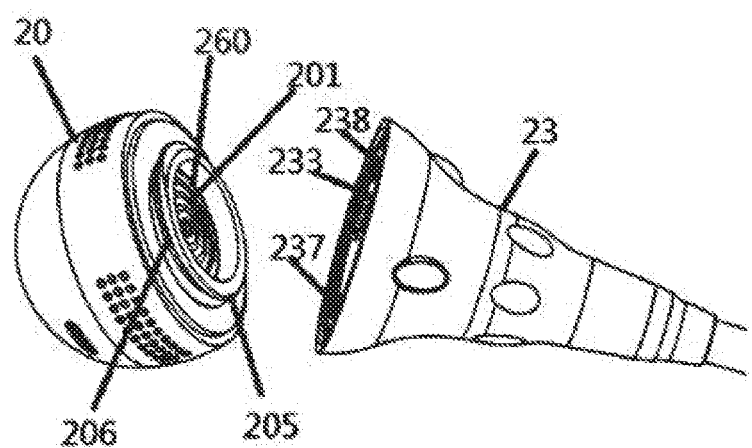
FIG. 5a is a structural schematic view of a discrete bioelectrical impedance identification device according to a fourth embodiment of the present disclosure.
Figure 5B:
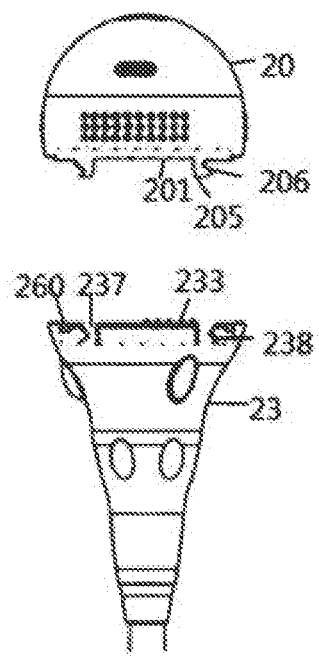
FIG. 5b is a side view of a discrete bioelectrical impedance identification device according to a fourth embodiment of the present disclosure.

Referring to FIG. 5a and FIG. 5b, they are schematic structural views of a discrete bioelectrical impedance identification device according to a fourth embodiment of the present disclosure.

As shown in FIGS. 5a and 5b, in the embodiment of the present disclosure, when the discrete bioelectrical impedance identification device uses a threaded connection as the detachable connection between the control shell 20 and the detection shell 23, the control shell 20 at its end connected to the detection shell 23 is provided with an annular protrusion 205. The detection shell 23 at its end connected to the control shell 20 is provided with an annular groove 237. Female threads 206 are provided on the outer wall of the annular protrusion 205, while male threads 238 are provided on the outer wall of the annular groove 237. The female threads 206 are matched with the male threads 238 so that the annular projection 205 can be screwed with the annular groove 237.

A conducting needle group 233 is arranged in the middle of the annular groove 237, and annular conducting strips 201 are arranged in the middle of the annular protrusion 205. The arranged position of the conducting needle group 233 is matched with the arrangement of the conducting strips 201 so that when the annular protrusion 205 is screwed with the annular groove 237, the conducting needle group 233 can abut against the conducting strips 201. Specifically, the conducting strips 201 are arranged in an annular shape and like one ring within another. A silicone sealing ring 260 is provided around the whole circumference of the annular groove 237 to prevent liquid from entering the inside of the shell when in use, making the operational procedure much safer.

The annular protrusion 205 is screwed into the annular groove 237 so that the conducting needle group 233 abuts against the conducting strips 201, and the device can be powered on for use. After use, the annular protrusion 205 is screwed out of the annular groove 237, the conducting needle group 233 is separated from the conducting strips 201, and the device is powered off. The detection module 2 is discarded after use, and the control module 1 is sterilized and retained for the next use.

On the one hand, the use of threaded connection makes the design simple and convenient, and the cost is low. On the other hand, the components used in the threaded link are less and are convenient to use.

Figure 6:
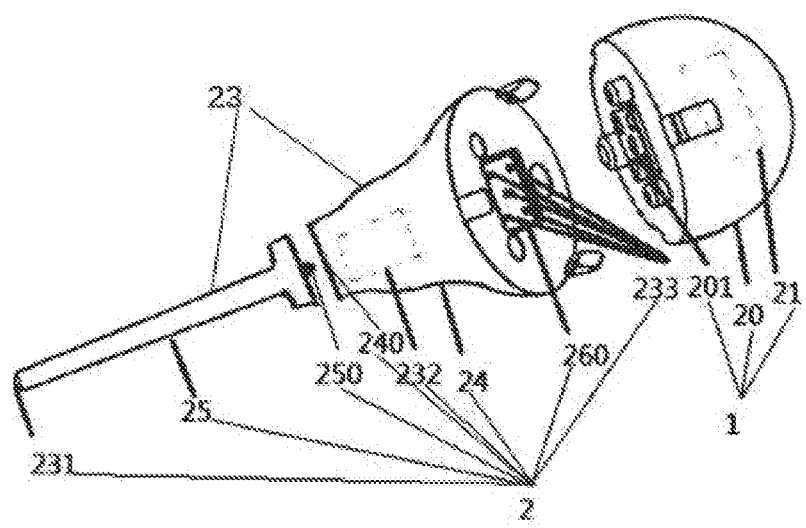
FIG. 6 is a structural schematic view of a discrete bioelectrical impedance identification device according to a fifth embodiment of the present disclosure.

Referring to FIG. 6, it is a schematic structural view of a discrete bioelectrical impedance identification device according to a fifth embodiment of the present disclosure.

As shown in FIG. 6, in the embodiment of the present disclosure, the detection shell 23 of the discrete bioelectrical impedance identification device includes a power supply shell 24 and a probe shell 25, the power supply shell 24 and the probe shell 25 being firmly connected in a detachable connection manner, thereby achieving multiple reuse of the power supply shell 24.

A power supply is provided inside the power supply shell 24. The power supply shell 24 can be in the form of a sphere, a hemisphere, an irregular sphere or other geometric shape having a receiving space. Specifically, the power supply 232 may be configured as a disposable battery, a lithium battery, or other power supply device for supplying power. The power supply shell 24 is provided with a conducting dot 240 which is partially exposed outside the power supply shell 24 and partially embedded in the power supply shell 24. The conducting dot 240 may be made of conductive material, which specifically, may be copper, iron or other conducting synthetic metal. The conducting dots 240 are electrically connected to the power supply 232 through conducting wires.

One end of the probe 231 is embedded in one end of the probe shell 25, and the other end of the probe 231 is exposed outside the probe shell 25. The probe is used for collecting the signals of electrical impedance characteristic. The tip of the probe 231 exposed outside the probe shell 25 may be tapered or flat.

The probe shell 25 has a receiving chamber for receiving the probe 231 therein, allowing itself to sleeve outside the probe 231. At its end away from the probe 231 the probe shell 25 is provided with a conducting needle 250. One end of the conducting needle 250 is electrically connected to the probe, and the other end is electrically connected to the power supply by abutting against the conducting dot 240. Specifically, the probe shell 25 can be cylindrical, flat, of flat curved rod shape or other geometric shapes.

The power supply shell 24 is firmly connected to the probe shell 25 in a detachable connection manner. When the power supply shell 24 is firmly connected to the probe shell 25, the conducting needle 250 abuts against the conducting dot 240. When the power supply shell 24 is separated from the probe shell 25, the conducting needle 250 is separated from the conducting dot 240.

The detachable connection between the power supply shell 24 and the probe shell 25 is one of a snap connection, a transverse insertion connection, or a threaded connection.

A discrete bioelectrical impedance identification device of the present disclosure divides the detection shell 23 into two parts, i.e. a power supply shell 24 and a probe shell 25. Both the power supply shell 24 and the probe shell 25 are disposable consumables, which have low producing cost and can be discarded directly after use. However, it is impossible for the power supply shell 24 to be exhausted after one use, so the present disclosure can make the power supply shell 24 be repeatedly used for several times. On the one hand, the utilization rate of the power supply shell 24 is increased, and on the other hand, waste is avoided and the production cost is reduced.

Figure 7:
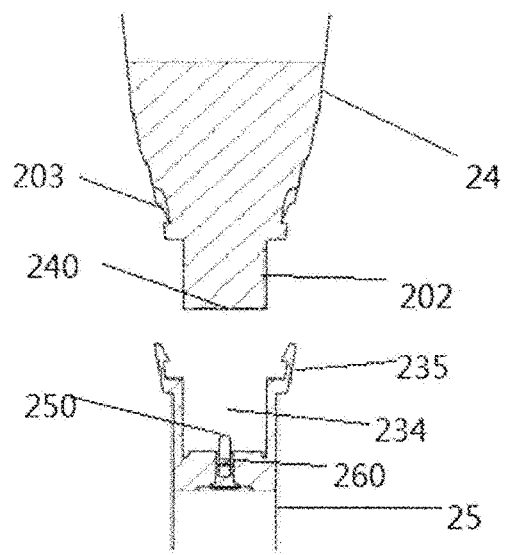
FIG. 7 is a structural schematic view of a discrete bioelectrical impedance identification device according to a sixth embodiment of the present disclosure.
Figure 8A:
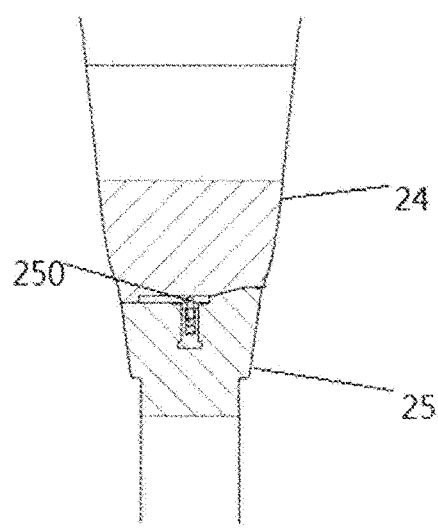
FIG. 8a is a structural side view of a discrete bioelectrical impedance identification device according to a seventh embodiment of the present disclosure.
Figure 8B:
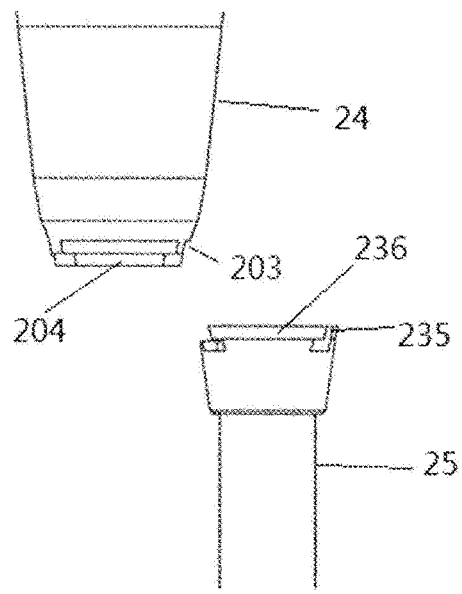
FIG. 8b is a structural schematic view of a discrete bioelectrical impedance identification device according to a seventh embodiment of the present disclosure.
Figure 8C:
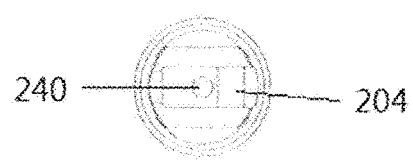
FIG. 8c is a bottom view of a power supply shell of a discrete bioelectrical impedance identification device according to a seventh embodiment of the present disclosure.
Figure 8D:
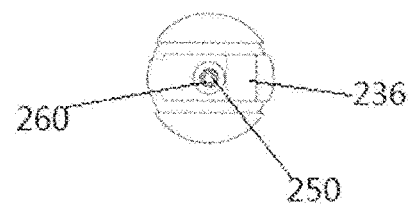
FIG. 8d is a top view of a probe shell of a discrete bioelectrical impedance identification device according to a seventh embodiment of the present disclosure.

Referring to FIG. 7, it is a schematic structural view of a discrete bioelectrical impedance identification device according to a sixth embodiment of the present disclosure.

As shown in FIG. 7, in the embodiment of the present disclosure, when the discrete bioelectrical impedance identification device adopts a snap connection as the detachable connection between the power supply shell 24 and the probe shell 25, the power supply shell 24 at its end connected to the probe shell 25 is provided with a protrusion 202. The probe shell 25 at its end connected to the power supply shell 24 is provided with a groove 234. The groove 234 is matched with the protrusion 202 in size so that the protrusion 202 can be inserted into the groove 234. The groove 234 and the protrusion 202 may be cylindrical, polygonal column or of other geometric shapes.

The conducting needle 250 is arranged at the bottom of the groove 234, while the conducting dot 240 is arranged at the top end of the protrusion 202. The arranged position of the conducting needle 250 is matched with the arrangement of the conducting dot 240 so that when the protrusion 202 is inserted into the groove 234, the conducting needle 250 can abut against the conducting dot 240. At least two snapping claws 235 are arranged around the top end of the groove 234, and at least two snapping slots 203 are provided at the back end of the protrusion 202. The snapping claws 235 are matched with the snapping slots 203 in shape and size so that the snapping claws 235 can be engaged in the snapping slots 203. Specifically, the snapping claws 235 are respectively provided with at least one snapping tooth, which is matched with the respective snapping slot 203 in shape.

The protrusion 202 is inserted into the groove 234, and the snapping claw 235 is snapped into the snapping slot 203. The conducting needle 250 abuts against the conducting dot 240. The device can be powered on, starting to work. After use, the snapping claws are separated from the snapping slots 203, the protrusion 202 is drawn out from the groove 234, the conducting needle 250 is separated from the conducting dot 240, and the device is powered off and stops working.

A silicone sealing ring 260 is arranged around the conducting needle 250 to prevent liquid from entering the interior of the shell to ensure the safety of the operational procedure.

The snap connection is adopted, as it is simple and convenient to operate, thereby saving connection time. The insertion of the protrusion 202 into the groove 234 has a certain function of fixing, thereby avoiding the instability of the connecting portion during the operation, and avoiding a surgical accident.

Referring to FIGS. 8a, 8b, 8c, and 8d, they are schematic structural views of a discrete bioelectrical impedance identification device according to a seventh embodiment of the present disclosure.

As shown in FIGS. 8a, 8b, 8c, and 8d, in the embodiment of the present disclosure, when the discrete bioelectrical impedance identification device uses a transverse insertion connection as the detachable connection between the power supply shell 24 and the probe shell 25, at its end connected to the probe shell 25 the power supply shell 24 is provided with at least one sliding rail 204, and at its end connected to the power supply shell 24 the probe shell 25 is provided with at least one sliding rail slot 236. The sliding rail slot 236 is matched with the sliding rail 204 in shape, size and amount so that the sliding rail 204 can be inserted into the sliding rail slot 236.

The conducting dot 240 is arranged in the middle of the surface of the sliding rail 204, and the conducting needle 250 is arranged in the middle of a surface of the sliding rail slot 236. The arranged position of the conducting needle 250 is matched with the arrangement of the conducting dot 240 so that when the sliding rail 204 is inserted into the sliding rail slot 236, the conducting needles 250 can abut against the conducting dot 240.

The sliding rail slot 236 is provided with a snapping claw 235 at the end. The sliding rail 204 is provided at its back end with a snapping slot 203. The snapping claw 235 is matched with the snapping slot 203 in shape, size and position, so that the snapping claw 235 can be engaged with the snapping slot 203.

The sliding rail 204 slides into the sliding rail slot 236, and the snapping claw 235 is snapped into the snapping slot 203. The conducting needle 250 abuts against the conducting dot 240, and the device can be powered on for use. After use, the snapping claw 235 is separated from the snapping slot 203, the sliding rail 204 slides out of the sliding rail slot 236, the conducting needle 250 is separated from the conducting dot 240, and the device stops working.

A silicone sealing ring 260 is arranged around the conducting needle 250 to prevent liquid from entering the interior of the shell to ensure the operational procedure much safer.

Through the transverse insertion connection, on the one hand, a side buckle is also designed for fixing in addition to the fixing of the sliding rail 204 and the sliding rail slot 236, which realizes a better fixing effect. On the other hand, the design of the sliding rail 204 and the sliding rail slot 236 makes it easier for the power supply shell 24 and the probe shell 25 to be aligned and engaged.

Figure 9:
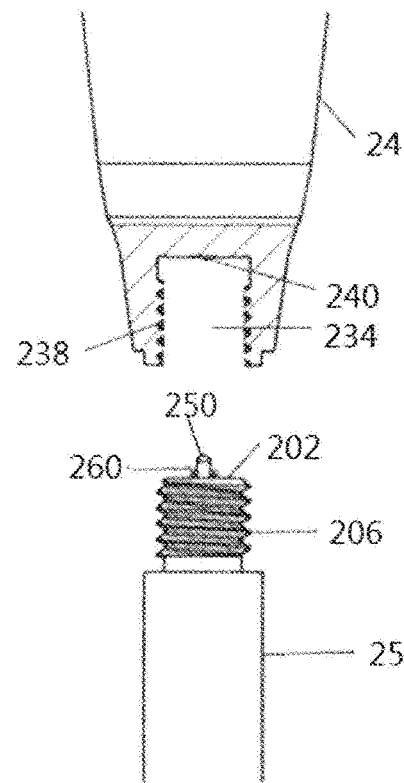
FIG. 9 is a structural schematic view of a discrete bioelectrical impedance identification device according to an eighth embodiment of the present disclosure.

Referring to FIG. 9, it is a schematic structural view of a discrete bioelectrical impedance identification device according to an eighth embodiment of the present disclosure.

As shown in FIG. 9, in the embodiment of the present disclosure, when the discrete bioelectrical impedance identification device uses a threaded connection as a detachable connection between the power supply shell 24 and the probe shell 25, at its end connected to the probe shell 25 the power supply shell 24 is provided with a groove 234, and at its end connected to the power supply shell 24 the probe shell 25 is provided with a protrusion 202. Female threads 206 are provided around the circumference of the protrusion 202, and male threads 238 are provided on a wall of the groove 234. The male threads 238 are matched with the female threads 206 so that the protrusion 202 can be threaded with the groove 234.

The conducting needle 250 is arranged at the bottom of the protrusion 202, and the conducting dot 240 is arranged at the top end of the groove 234. The arranged position of the conducting needle 250 is matched with the arrangement of the conducting dot 240 so that when the protrusion 202 is screwed into the groove 234, the conducting needle 250 can abut against the conducting dot 240.

A silicone sealing ring 260 is arranged around the conducting needle 250 to prevent liquid from entering the interior of the shell to make the operational procedure much safer.

The protrusion 202 is screwed into the groove 234 so that the conducting needle 250 abuts against the conducting dot 240, and the device can be powered on for use. After use, the protrusion 202 is screwed out of the groove 234, the conducting needle 250 is separated from the conducting dot 240, and the device is powered off. The probe shell 25 is discarded after use, and the power supply shell 24 and the control shell 20 are sterilized and retained for the next use.

On the one hand, the use of threaded connection makes the design simple and convenient, and makes the cost low. On the other hand, the components used in the threaded link are less and convenient to use.

In the description of the present specification, references or expressions like "one embodiment", "an alternative embodiment", "an optional embodiment", "example", "specific example" or "some examples" etc. means specific features, structures, materials or characteristics described in combination with an embodiment or example are included in at least one embodiment or example of the present disclosure. In the present specification, the schematic description of the above terms does not necessarily indicate the same embodiment or example. Furthermore, the specific features, structures, materials, or characteristics described may be combined in a suitable manner in any one or more embodiments or examples.

It should be understood that, the above-described embodiments of the present disclosure are intended to be illustrative only or explain the principle of the present disclosure, and not to limit the present disclosure. Therefore, any modifications, equivalent substitutions, improvements, etc., which are made without departing from the spirit and scope of the present disclosure, are intended to be included within the scope of the present disclosure. Besides, the appended claims of the present disclosure are intended to cover all such modifications and modifications falling into the scope, boundary, or equivalents of scope and boundary of the appended claims.

The invention claimed is:

1. A discrete bioelectrical impedance identification device, comprising:
    a control module (1) including a control shell (20) and a control processing circuit (21) arranged inside the control shell (20), wherein the control shell (20) is provided with conducting strips (201) which are partially exposed out of the control shell, partially embedded in the control shell (20), and electrically connected to the control processing circuit (21);
    a detection module (2) firmly connected to the control shell (20) in a detachable connection manner; wherein the detection module (2) comprises: a detection shell (23), a probe (231) embedded in one end of the detection shell (23), and a power supply (232) embedded in another end of the detection shell (23);
    wherein the probe (231) is partially exposed out of the detection shell (23) and used for collecting signals of electrical impedance characteristics;
    wherein the detection shell (23) has a receiving chamber for receiving the probe (231) therein, allowing itself to sleeve outside the probe (231), and has, at its end away from the probe (231), a power supply receiving chamber for receiving the power supply (232);
    wherein the detection shell (23) is provided with a conducting needle group (233) on the detection shell at the end provided with the power supply (232), the conducting needle group (233) being partially exposed out of the detection shell and one end of the conducting needle group (233) being electrically connected to the power supply (232);
    wherein the control shell (20) is configured to be firmly connected to the detection shell (23) in the detachable connection manner such that the control shell (20) is firmly connected to the detection shell (23), the conducting needle group (233) abuts against the conducting strips (201), and such that when the control shell (20) is separated from the detection shell (23), the conducting needle group (233) is separated from the conducting strips (201),
    wherein the detection shell (23) comprises: a power supply shell (24) and a probe shell (25), wherein the power supply (232) is arranged in the power supply shell (24), the power supply shell (24) is provided with a conducting dot (240) partially exposed out of the power supply shell (24) and partially embedded in the power supply shell (24), and the conducting dot (240) is electrically connected to the power supply (232);
    wherein at its end connected to the power supply shell (24) the probe shell (25) is provided with a conducting needle (250) partially exposed out of the probe shell (25), wherein one end of the conducting needle (250) is electrically connected to the probe (231); and
    wherein the probe shell (25) is configured to be firmly connected to the power supply shell (24) in a detachable connection manner such that when the probe shell (25) is firmly connected to the power supply shell (24), the conducting needle (250) abuts against the conducting dot (240), and such that when the probe shell (25) is separated from the power supply shell (24), the conducting needle (250) is separated from the conducting dot (240).

2. The device according to claim 1, wherein the detachable connection manner between the control shell and the detection shell is one of a snap connection, a transverse insertion connection, or a threaded connection.

3. The device according to claim 2, wherein the snap connection is used as the detachable connection manner between the control shell (20) and the detection shell (23),
    at its end connected to the detection shell (23) the control shell (20) is provided with a protrusion (202);
    at its end connected to the control shell (20) the detection shell (23) is provided with a groove (234);
    the groove (234) is matched with the protrusion (202) in size so that the protrusion (202) can be inserted into the groove (234);
    the conducting needle group (233) is arranged at a bottom of the groove (234), the conducting strips (201) are arranged at a top end of the protrusion (202), and the conducting needle group (233) is matched with the conducting strips (201) such that when the protrusion (202) is inserted into the groove (234), the conducting needle group (233) abuts against the conducting strips (201);
    snapping slots (203) are provided around the control shell (20) at its end connected to the detection shell (23);
    snapping claws (235) are provided around the detection shell (23) at its end connected to the control shell (20); and
    the snapping claws (235) are matched with the snapping slots (203) in shape and size so that the snapping claws (235) can be engaged with the snapping slots (203).

4. The device according to claim 2, wherein the transverse insertion connection is used as the detachable connection manner between the control shell (20) and the detection shell (23),
    at its end connected to the detection shell (23) the control shell (20) is provided with a sliding rail (204);
    at its end connected to the control shell (20) the detection shell (23) is provided with a sliding rail slot (236);
    the sliding rail (204) is matched with the sliding rail slot (236) in size and shape so that the sliding rail (204) can be snapped into the sliding rail slot (236);
    the conducting needle group (233) is arranged at a bottom of the sliding rail slot (236), and the conducting strips (201) are arranged at a top of the sliding rail (204), the conducting needle group (233) is matched with the conducting strips (201) such that when the sliding rail (204) is inserted into the sliding rail slot (236), the conducting needle group (233) abuts against the conducting strips (201); and a snapping claw (235) is provided at one end of the sliding rail slot (236), and a snapping slot (203) is provided at one end of the sliding rail (204), wherein the snapping claw (235) is matched with the snapping slot (203) in shape, size and position so that the snapping claw (235) can be engaged with the snapping slot (203).

5. The device according to claim 2, wherein the threaded connection is used as the detachable connection manner between the control shell (20) and the detection shell (23),
- at its end connected to the detection shell (23) the control shell (20) is provided with an annular protrusion (205);
- at its end connected to the control shell (20) the detection shell (23) is provided with an annular groove (237);
- female threads (206) are provided on an outer wall of the annular protrusion (205), and male threads (23) are provided on an outer wall of the annular groove (237), wherein the female threads (206) are matched with the male threads (238) so that the annular protrusion (205) can be screwed with the annular groove (237);
- the conducting needle group (233) is arranged in a middle of the annular groove (237), and the annular conducting strips (201) are arranged in a middle of the annular protrusion (205), wherein the conducting needle group (233) is matched with the conducting strips (201) such that when the annular protrusion (205) is screwed with the annular groove (237), the conducting needle group (233) abuts against the conducting strips (201).

6. The device according to claim 1, wherein the detachable connection manner between the power supply shell and the probe shell is one of a snap connection, a transverse insertion connection, or a threaded connection.

7. The device according to claim 6, wherein the snap connection is used as the detachable connection manner between the power supply shell (24) and the probe shell (25),
- at its end connected to the probe shell (25) the power supply shell (24) is provided with a protrusion (202);
- at its end connected to the power supply shell (24) the probe shell (25) is provided with a groove (234);
- the groove (234) is matched with the protrusion (202) in size so that the protrusion (202) can be inserted into the groove (234);
- the conducting needle (250) is arranged at a bottom of the groove (234), the conducting dot (240) is arranged at a top end of the protrusion (202), and the conducting needle (250) is matched with the conducting dot (240) such that when the protrusion (202) is inserted into the groove (234), the conducting needle (250) abuts against the conducting dot (240); and
- snapping claws (235) are provided around the groove (234) at its top end, and the protrusion (202) is provided at its back end with snapping slots (203), wherein the snapping claws (235) are matched with the snapping slots (203) in size and shape so that the snapping claws (235) can be engaged with the snapping slots (203).

8. The device according to claim 6, wherein the transverse insertion connection is used as the detachable connection manner between the power supply shell (24) and the probe shell (25),
- at its end connected to the probe shell (25) the power supply shell (24) is provided with a sliding rail (204);
- at its end connected to the power supply shell (24) the probe shell (25) is provided with a sliding rail slot (236);
- the sliding rail slot (236) is matched with the sliding rail (204) in size and position so that the sliding rail (204) can be inserted into the sliding rail slot (236);
- the conducting needle (250) is arranged in a middle of the sliding rail slot (236), and the conducting dot (240) is arranged in a middle of the sliding rail (204), wherein the conducting needle (250) is matched with the conducting dot (240) such that the conducting needle (250) abuts against the conducting dot (240) when the sliding rail (204) is inserted into the sliding rail slot (236); and
- a snapping claw (235) is provided at one end of the sliding rail slot (236), and a snapping slot (203) is provided at a back end of sliding rail (204), wherein the snapping claw (235) is matched with the snapping slot (203) in shape, size and position so that the snapping claw (235) can be engaged with the snapping slot (203).

9. The device according to claim 6, wherein the threaded connection is used as the detachable connection manner between the power supply shell (24) and the probe shell (25),
- at its end connected to the probe shell (25) the power supply shell (24) is provided with a groove (234);
- at its end connected to the power supply shell (24) the probe shell (25) is provided with a protrusion (202);
- female threads (206) are provided on an outer circumference of the protrusion (202), and male threads (238) are provided on a wall of the groove (234), wherein the female threads (206) are matched with the male threads (238) so that the protrusion (202) can be screwed with the groove (234); the conducting needle (250) is arranged at a top of the protrusion (202), the conducting dot (240) is arranged at a bottom of the groove (234), and the conducting needle (250) is matched with the conducting dot (240) such that the conducting needle (250) abuts against the conducting dot (240) when the protrusion (202) is screwed into the groove (234).

* * * * *